United States Patent
Wu et al.

(10) Patent No.: US 11,566,204 B2
(45) Date of Patent: Jan. 31, 2023

(54) PHOSPHOLIPASE C AND ENCODING GENE THEREOF

(71) Applicant: Wilmar (Shanghai) Biotechnology Research & Development Center Co., Ltd., Shanghai (CN)

(72) Inventors: Wei Wu, Shanghai (CN); Xiaojun Dai, Shanghai (CN); Haisheng Cao, Shanghai (CN); Qiwen Niu, Shanghai (CN)

(73) Assignee: Wilmar (Shanghai) Biotechnology Research & Development Center Co., Ltd., Shanghai (CN)

( * ) Notice: Subject to any disclaimer, the term of this patent is extended or adjusted under 35 U.S.C. 154(b) by 147 days.

(21) Appl. No.: 16/771,447

(22) PCT Filed: Dec. 10, 2018

(86) PCT No.: PCT/CN2018/120026
§ 371 (c)(1),
(2) Date: Jun. 10, 2020

(87) PCT Pub. No.: WO2019/114645
PCT Pub. Date: Jun. 20, 2019

(65) Prior Publication Data
US 2021/0071102 A1    Mar. 11, 2021

(30) Foreign Application Priority Data

Dec. 12, 2017 (CN) .......................... 201711317381.6

(51) Int. Cl.
C11B 3/00 (2006.01)
C12N 9/16 (2006.01)
C12N 15/81 (2006.01)

(52) U.S. Cl.
CPC ............... *C11B 3/003* (2013.01); *C12N 9/16* (2013.01); *C12N 15/815* (2013.01); *C12Y 301/04003* (2013.01)

(58) Field of Classification Search
CPC .. C11B 3/003; C11B 3/00; C12N 9/16; C12N 15/815; C12Y 301/04003
See application file for complete search history.

(56) References Cited

U.S. PATENT DOCUMENTS 10,738,288 B2 * 8/2020 Xuan ............. C12Y 301/04003
2018/0362942 A1 * 12/2018 Xuan ....................... C11B 3/003

FOREIGN PATENT DOCUMENTS

| CN | 101558154 A | 10/2009 |
|---|---|---|
| CN | 104630174 A | 5/2015 |
| CN | 106884009 A | 6/2017 |
| WO | 2017101801 A1 | 6/2017 |

OTHER PUBLICATIONS

Whisstock et al. Quaterly Reviews of Biophysics, 2003, "Prediction of protein function from protein sequence and structure", 36(3): 307-340.*
Kisselev L., Polypeptide release factors in prokaryotes and eukaryotes: same function, different structure. Structure, 2002, vol. 10: 8-9.*
Chenna, R., et al. "Multiple sequence alignment with the Clustal series of programs." Nucleic acids research 31.13 (2003): 3497-3500.
Deshpande, M. V. "Ethanol production from cellulose by coupled saccharification/fermentation using *Saccharomyces cerevisiae* and cellulase complex from *Sclerotiun rolfsii* UV-8 mutant." Applied biochemistry and biotechnology 36.3 (1992): 227.
Higgins, D. G. et al. "Fast and sensitive multiple sequence alignments on a microcomputer." Bioinformatics 5.2 (1989): 151-153.
Thompson, J. D., et al. "CLUSTAL W: improving the sensitivity of progressive multiple sequence alignment through sequence weighting, position-specific gap penalties and weight matrix choice." Nucleic acids research 22.22 (1994): 4673-4680.
Hough., E., et al. (1989) "High-resolution (1.5A) crystal structure of phospholipase C from Bacillus cereus.", Nature. 338:357-60.
International Searching Authority. International Search Report and Written Opinion for application PCT/CN2018/120026, dated Mar. 12, 2019. With translation.
Johansen, T., et al. (1988). "Cloning and sequencing of the gene encoding the phosphatidylcholine-preferring phospholipase C of Bacillus cereus." Gene 65(2):293-304.
Rice, P. et al. "EMBOSS: the European molecular biology open software suite." (2000): 276-277.
Elena et al., B. Cereus Phospholipase C Engineering for Efficient Degumming of Vegetable Oil, Process Biochemistry, 2017, 54:67-72.
Lyu et al., Recent Research Progress with Phospholipase C from Bacillus Cereus, Biotechnology Letters, 2016, 38:23-31.
European Patent Office, Extended Search Report, Application No. 18889610.4, dated Jul. 16, 2021, 9 pages.

* cited by examiner

*Primary Examiner* — Iqbal H Chowdhury
(74) *Attorney, Agent, or Firm* — Quarles & Brady LLP

(57) ABSTRACT

According to the present disclosure, on the basis of all existing mutations, the tenth glycine of a BC-PC-PLC is mutated into aspartic acid, a specific enzyme activity thereof is 83% higher than that of a sequence before the mutation, and protein expression and degumming activity of unit enzyme activity do not change, so as to further reduce manufacturing costs.

7 Claims, 2 Drawing Sheets
Specification includes a Sequence Listing.

PHOSPHOLIPASE C AND ENCODING GENE THEREOF

CROSS-REFERENCE TO RELATED APPLICATIONS

This application represents the U.S. national stage entry of International Application No. PCT/CN2018/120026 filed Dec. 10, 2018, which claims priority to Chinese Patent Application No. 201711317381.6 filed Dec. 12, 2017, the disclosure of which is incorporated herein by reference in its entirety and for all purposes.

REFERENCE TO A SEQUENCE LISTING SUBMITTED VIA EFS-WEB

The content of the ASCII text file of the sequence listing named "850766-00092-ST25.txt" which is 7.15 KB in size was created on Jun. 5, 2020 and electronically submitted via EFS-Web herewith, the application is incorporated herein by reference in its entirety.

TECHNICAL FIELD

The disclosure relates to a new phospholipase C and encoding gene thereof. The disclosure also relates to vectors and host cells comprising the gene. In addition, the disclosure also relates to methods of preparing the phospholipase C and uses of the phospholipase C.

BACKGROUND

In the manufacture of vegetable edible oils, crude oil extracted from oilseeds through preliminary crushing and leaching generally contains impurities such as proteins, sterols, phospholipids, pigments, trace metals, and free fatty acids, which affect the quality of edible oils and make the oil inedible. Therefore, oil refining is required. Degumming is a very important part of vegetable oil refining. Recently, the enzymatic degumming technology has received attention due to its mild reaction conditions, high refining yield, environmental-friendliness, and having wide range of applications.

Phospholipase is an enzyme widely present in animals, plants, and microorganisms that can specifically hydrolyze glycerophospholipids. Based on different reaction sites of phospholipase on phospholipids, phospholipase can be divided into phospholipase A1 (PLA1), phospholipase A2 (PLA2), phospholipase B (PLB), phospholipase C (PLC) and phospholipase D (PLD). At present, the degumming process of vegetable oil mainly uses PLA1, PLA2, PLB and PLC. PLA1 and PLA2 can specifically hydrolyze the ester bond at Sn-1 or Sn-2 of a phospholipid and generate the corresponding lysophospholipid; PLB can hydrolyze both the ester bond at Sn-1 and Sn-2 and generate the corresponding glyceroylphospholipid. Both lysophospholipids and glyceroylphospholipids are highly hydrophilic and can be easily removed by hydration. PLC can specifically hydrolyze the phosphoglyceride bond at Sn-3 of a phospholipid and generate the corresponding diacylglycerol (DAG) and phosphatidic acids, wherein DAG, as a neutral oil, will not be removed during the subsequent refining, which can effectively improve the oil yield after refining.

Phosphatidylcholine-phosphatase C of *Bacillus cereus* (BC-PC-PLC) is a phospholipase C studied earlier. BC-PC-PLC has a total length of 283 amino acids, including a signal peptide of 24 amino acids and a pro-peptide of 14 amino acids, and the mature peptide of BC-PC-PLC has 245 amino acids (Johansen, T., Holm, T., Guddal, P. H., Sletten, K., Haugli, F. B., Little, C. (1988). "Cloning and sequencing of the gene encoding the phosphatidylcholine-preferring phospholipase C of *Bacillus cereus*." *Gene* 65(2):293-304). The crystal structure of BC-PC-PLC has been reported, which consists of multiple helical domains, with a catalytic site at D55, and at least three $Zn^{2+}$ binding sites (Hough., E., Hansen, L. K., Birknes, B., Jynge, K., Hansen, S., Hordvik, A., Little, C., Dodson, E., Derewenda, Z. (1989) "High-resolution (1.5A) crystal structure of phospholipase C from *Bacillus cereus*.", *Nature*. 338:357-60).

In previous researches, CN104630174A increased the enzyme activity of BC-PC-PLC by 16-fold as compared with the original sequence by mutation of three glycosylation sites of BC-PC-PLC, i.e., N63, N131 and N134, to aspartic acid, serine and aspartic acid respectively; CN2016/110030 provide a variant having higher phospholipase activity under lower zinc sulfate conditions by mutation of Y56 to histidine based on the glycosylation site mutated version, wherein, as compared to the glycosylation site mutated version, the variant's enzyme activity increased 7-fold under 10 μM zinc sulfate conditions. In order to further improve the degumming efficiency of the phospholipase C, the present application continues to mutate the phospholipase C, hoping to obtain more efficient phospholipase C mutants having much higher enzyme activity, and to improve the degumming efficiency and diacylglycerol (DAG) yield during the degumming process.

SUMMARY

According to the present disclosure, on the basis of all mutations as described above, the glycine at amino acid 10 of BC-PC-PLC is mutated into aspartic acid, wherein the specific enzyme activity of the mutated BC-PC-PLC is 83% higher than that of a sequence before the mutation, and degumming ability of per unit enzyme activity and protein expression is not changed, so as to further reduce production costs.

The present application relates to a phospholipase C, comprising or consisting of a sequence selected from: (a) the amino acid sequence of SEQ ID NO: 4, and (b) the sequence of (a) having at least one amino acid deleted, substituted, or inserted, and still retaining the function of SEQ ID NO: 4, wherein the substitution is preferably a conservative substitution of the amino acid.

The application also relates to a phospholipase C derived from *Bacillus cereus*, comprising an amino acid sequence selected from:

the amino acid sequence having at least 90%, preferably at least 95%, more preferably at least 98% homology to the sequence of SEQ ID NO: 4, with amino acid residue at position 10 being aspartic acid at; preferably, the amino acid residue at position 56 of the amino acid sequence is histidine, the amino acid residue at position 63 of the amino acid sequence is aspartic acid, the amino acid residue at position 131 of the amino acid sequence is serine, and/or the amino acid residue at position 134 of the amino acid sequence is aspartic acid.

The disclosure also relates to a nucleic acid molecule selected from: (a) a nucleotide sequence encoding the phospholipase C of the present disclosure; and (b) a nucleotide sequence complementary to the nucleotide sequence of (a). In one embodiment, the nucleotide sequence of the nucleic acid molecule is described in SEQ ID NO: 3.

The disclosure also relates to a vector comprising the nucleic acid molecule described above. The disclosure also relates to a host cell comprising the nucleic acid molecule or the vector described above. The host cell may be selected from a bacterial cell, a fungal cell, preferably a yeast cell, a mammalian cell, an insect cell and a plant cell. In one embodiment, the host cell is a *Pichia pastoris* cell.

The disclosure also relates to a method of producing phospholipase C, comprising expressing a nucleic acid molecule encoding the phospholipase C of the present disclosure in a host cell, and recovering resultant polypeptides.

The disclosure also relates to use of the phospholipase C of the present disclosure in oil degumming.

The disclosure also relates to a composition comprising the phospholipase C of the present disclosure or the fermentation broth, fermentation supernatant and/or fermentation concentrate, of the host cell of the present disclosure.

The disclosure also relates to the fermentation broth, fermentation supernatant or fermentation concentrate, of the host cell of the present disclosure.

The disclosure also relates to a method for oil degumming, the method uses the phospholipase C of the present disclosure or the composition of the present disclosure or the fermentation broth, fermentation supernatant and/or fermentation concentrate, of the host cell of the present disclosure for the oil degumming.

BRIEF DESCRIPTION OF SEQUENCES

Figure 1:
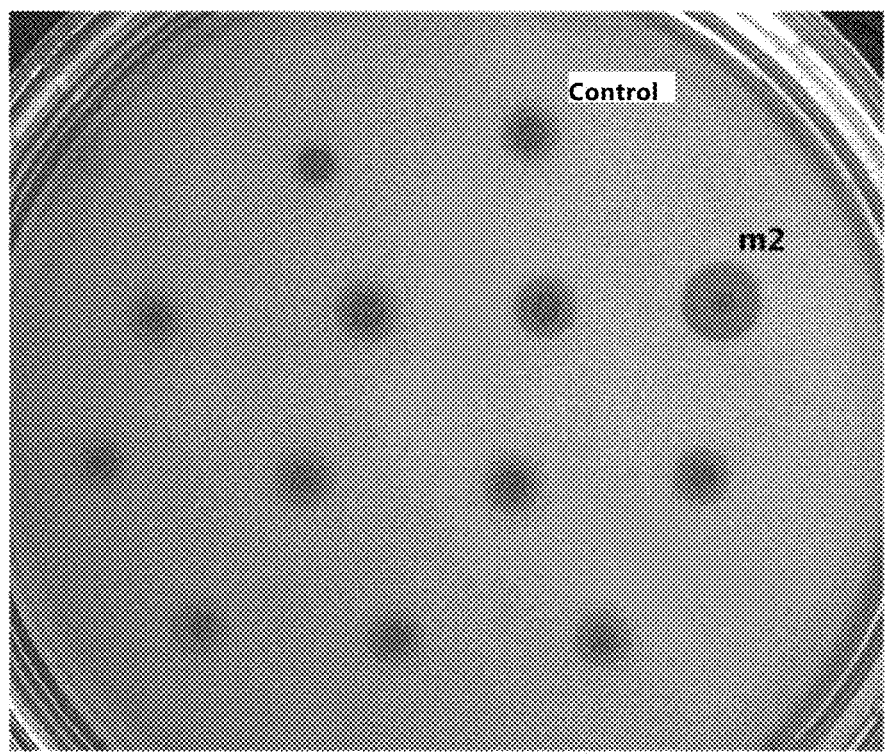
FIG. 1 is a phospholipase C variant screening plate diagram, using soybean phospholipid as substrate.

SEQ ID NO: 1 is the coding DNA sequence of mPLC, the phospholipase C having mutations of Y56H, N63D, N131S, N134D.

SEQ ID NO: 2 is the amino acid sequence of mPLC, the phospholipase C having mutations of Y56H, N63D, N131S, N134D.

SEQ ID NO: 3 is the coding DNA sequence of m2PLC, the phospholipase C having mutations of G10D, Y56H, N63D, N131S, N134D.

SEQ ID NO: 4 is the amino acid sequence of m2PLC, the phospholipase C having mutations of G10D, Y56H, N63D, N131S, N134D.

SEQ ID NOs: 5 and 6 are the sequences of primers PLC-F/PLC-R.

DETAILED DESCRIPTION

The present application relates to a phospholipase C, comprising or consisting of a sequence selected from:
(a) the amino acid sequence of SEQ ID NO: 4, and
(b) the sequence of (a) having at least one amino acid deleted, substituted, or inserted, and still retaining the function of SEQ ID NO: 4, wherein the substitution is preferably a conservative substitution of the amino acid.

In one embodiment, the sequence of the phospholipase C of the present disclosure is shown as SEQ ID NO: 4. In addition, SEQ ID NO: 4 of the present disclosure may also have one or more, e.g. 1-10, 1-9, 1-8, 1-7, 1-6, 1-5, 1-4, 1-3, 1-2 amino acid residues additions, deletions, or substitutions, resulting in silence changes or functionally equivalent enzymes. With the enzyme activity maintained, the amino acid substitutions can be designed based on the similarity of the residues in polarity, charge, solubility, hydrophilicity, hydrophobicity, and/or amphiphilicity. For example, negatively charged amino acids include aspartic acid and glutamic acid; positively charged amino acids include lysine and arginine; amino acids having similar hydrophilicity and a non-charged polar head include leucine, isoleucine, valine, glycine, alanine, asparagine, glutamine, serine, threonine, phenylalanine and tryptophan.

Conservative substitutions can be made according to the following table. Amino acids in the same row of the second column can be substituted for each other; preferably, amino acids in the same row of the third column can be substituted for each other:

| Aliphatic amino acid | Non-polar | G, A, P |
| | | I, L, V |
| | Polar and non-charged | C, S, T, M |
| | | N, Q |
| | Polar and charged | D, E |
| | | K, R |
| Aromatic amino acid | | H, F, W, Y |

The disclosure comprising a sequence obtained by deleting, adding, or conservatively substituting one or more amino acid residues of the sequence of SEQ ID NO: 4, which still retains its activity. It should be considered as equivalent to SEQ ID NO: 4 and receive patent protection.

The disclosure also relates to a nucleic acid molecule selected from:
(a) a nucleotide sequence encoding phospholipase C of the present disclosure; and
(b) a nucleotide sequence partially or completely complementary to the nucleotide sequence of (a).

In one embodiment, the nucleotide sequence of the nucleic acid molecule is described in SEQ ID NO: 3.

Those skilled in the art will understand that, due to the degeneracy of the genetic code, different nucleotide sequences can encode the same enzyme. In addition, it can be appreciated that those skilled in the art can make nucleotide substitutions which do not affect the activity of the enzyme encoded by the nucleotide sequence of the present disclosure through conventional techniques, and this indicates the codon preference of the specific host organism used to express the enzyme of the present disclosure.

The present disclosure also includes sequences having identity to SEQ ID NOs: 3 and 4 described herein. A proper nucleic acid or amino acid sequence has at least about 50%, preferably at least 60%, more preferably at least 70%, more preferably at least 80%, even more preferably at least 85%, even more preferably at least 90%, even more preferably at least 95%, most preferably at least 98% identity to SEQ ID NOs: 3 and 4 present herein. It should be considered as equivalent to SEQ ID NOs: 3 and 4 and receive patent protection.

Particularly, the application also relates to a phospholipase C derived from *Bacillus cereus*, comprising an amino acid sequence selected from:
the amino acid sequence having at least 90%, preferably at least 95%, more preferably at least 98% identity to the sequence of SEQ ID NO: 4, with amino acid residue at position 10 being aspartic acid at; preferably, the amino acid residue at position 56 of the amino acid sequence is histidine, the amino acid residue at position 63 of the amino acid sequence is aspartic acid, the amino acid residue at position 131 of the amino acid sequence is serine, and/or the amino acid residue at position 134 of the amino acid sequence is aspartic acid.

Percent identity is the relationship between two or more polypeptide sequences or between two or more polynucleotide sequences, and the relationship is determined by comparing the sequences. In the art, "identity" also refers to the correlation degree of sequences between polypeptide or polynucleotide sequences, which is determined by the alignment of linear sequences, depending on the specific circumstances. "Identity" can be easily calculated by known methods including, but not limited to, the following methods: Computational Molecular Biology (Lesk, A. M., Ed.) Oxford University Press, NY (1988); Biocomputing: Informatics and Genome Projects (Smith, D. W., Ed.) Academic Press, NY (1993); Computer Analysis of Sequence Data, Part I (Griffin, A. M., and Griffin, H. G., Eds.) Humana Press, NJ (1994); Sequence Analysis in Molecular Biology (von Heinje, G., ed.) Academic Press (1987); and Sequence Analysis Primer (Gribskov, M. and Devereux, J., eds.) Stockton Press, NY (1991). The methods of determining identity are coded in publicly available computer programs. Sequence alignment and percent identity calculation can be performed by the Megalign program of LASERGENE bioinformatics computing software package (DNASTAR Inc., Madison, Wis.), AlignX program of Vector NTI v. 7.0 (Informax, Inc., Bethesda, Md.), or EMBOSS Open Software Suite (EMBL-EBI; Rice et. al, *Trends in Genetics* 16, (6):276-277 (2000)). Sequence multiple alignments can be performed using the Clustal alignment method (i.e. CLUSTALW; e.g. version 1.83) (Higgins and Sharp, *CABIOS*, 5: 151-153 (1989); Higgins et al., *Nucleic Acids Res.* 22: 4673-4680 (1994); and Chenna et al., *Nucleic Acids Res* 31 (13): 3497-500 (2003)), which were obtained from European Molecular Biology Laboratory via the European Bioinformatics Institute, with default parameters.

The present disclosure also provides a vector comprising the nucleic acid molecule, and a host cell comprising the nucleic acid molecule or the vector.

The term "vector" refers to extrachromosomal elements that usually harbor genes that are not part of the central metabolism of the cell, and are often in the form of circular double-stranded DNA molecules. Such elements may be genomic integration sequences, phage or nucleotide sequences, linear or circular single or double stranded DNAs or RNAs, autonomously replicating sequences derived from any source, many of which have been joined or recombined into a specific construct that is capable of introducing the promoter fragment and DNA sequence of the designated gene product into cells together with an appropriate 3' untranslated sequence.

The genes and gene products of the sequences of the present disclosure can be in heterologous host cells, such as bacterial cells, fungal cells, such as yeast cells, mammalian cells, insect cells, and plant cells. The heterologous host cells used to express the nucleic acid molecule of the present disclosure may be a microbial host that exists in the family of fungi or bacteria and grows within a wide range of temperatures, pH values, and solvent tolerance. For example, it is contemplated that any bacteria, yeast and filamentous fungi can be a suitable host for expressing the nucleic acid molecules of the disclosure. Examples of host strains include, but are not limited to, bacterial, fungal or yeast species such as *Pichia* sp., *Aspergillus* sp., *Trichoderma* sp., *Saccharomyces* sp., *Phaffia* sp., *Kluyveromyces* sp., *Yarrowia* sp., *Candida* sp., *Hansenula* sp., *Salmonella* sp., *Bacillus* sp., *Acinetobacter* sp., *Zymomonas* sp., *Agrobacterium* sp., *Erythrobacter* sp., *Chlorobium* sp., *Chromatium* sp., *Flavobacterium* sp., *Cytophaga* sp., *Rhodobacter* sp., *Rhodococcus* sp., *Streptomyces* sp., *Brevibacterium* sp., *Corynebacteria* sp., *Mycobacterium* sp., *Deinococcus* sp., *Escherichia* sp., *Erwinia* sp., *Pantoea* sp., *Pseudomonas* sp., *Sphingomonas* sp., *Methylomonas* sp., *Methylobacter* sp., *Methylococcus* sp., *Methylosinus* sp., *Methylomicrobium* sp., *Methylocystis* sp., *Alcaligenes* sp., *Synechocystis* sp., *Synechococcus* sp., *Anabaena* sp., *Thiobacillus* sp., *Methanobacterium* sp., Gram *Klebsiella* sp. and *Myxococcusl* sp. In one embodiment, the host cell is a *Pichia pastoris* cell.

Vectors that can be used to transform the above-mentioned host cells are well known in the art. Generally, a vector contains sequences that guide the transcription and translation of related genes, sequences of optional markers, and sequences that allow autonomous replication or chromosomal integration. A suitable vector contains gene 5' region controlling transcription initiation and DNA fragment 3' region controlling transcription termination.

The disclosure also relates to a method of producing phospholipase C, comprising expressing a nucleic acid molecule encoding the phospholipase C of the present disclosure in a host cell, and recovering resultant polypeptides.

Various cultivation methods can be applied to prepare the enzyme of the present disclosure. For example, large-scale production of specific gene products by recombinant microbial hosts can be performed by batch, feed-batch, and continuous culture.

Batch and feed-batch culture methods are commonly used and well-known in the art, and examples can be found in: "Thomas D. Brock in Biotechnology: A Textbook of Industrial Microbiology", Second Edition, Sinauer Associates, Inc., Sunderland, Mass. (1989), and Deshpande, Mukund V., *Appl. Biochem. Biotechnol.*, 36:227-234 (1992).

The commercial production of the enzyme of the present disclosure can also be carried out by continuous culture. Continuous culture is an open system in which the prepared medium is continuously added to the bioreactor, while equal amount of conditioned medium is simultaneously removed for processing. Generally, continuous culture keeps the cells at a constant high liquid phase density in which the cells are mainly in the logarithmic growth phase. Alternatively, continuous culture can be performed with immobilized cells, wherein carbon sources and nutrients are continuously added, while valuable products, by-products, or waste are continuously removed from the cell mass. Cell immobilization can be performed using various solid supports consisting of natural materials and/or synthetic materials.

Recovery of the desired enzyme from batch fermentation, feed-batch fermentation, or continuous culture can be accomplished by any method known to those skilled in the art. For example, when producing enzymes in cells, the cell slurry is separated from the culture medium by centrifugation or membrane filtration, and optionally washed with water or an aqueous buffer at a desired pH, and then the cell slurry in the aqueous buffer at the desired pH is suspended and homogenized to obtain a cell extract containing the desired enzyme.

The disclosure also relates to a composition comprising the fermentation broth, fermentation supernatant and/or fermentation concentrate of the phospholipase C of the disclosure or the host cell of the disclosure. The enzyme composition of the present disclosure may be in any form suitable for use, for example, crude fermentation broth with or without cells, cell lysate with or without cell debris, purified or partially purified enzyme composition, or host cells as a source of enzymes. The enzyme composition may be in the form of dry powder or granules, dust-free granules, liquid, stabilized liquid, or stabilized protected enzyme. The liquid enzyme composition can be stabilized according to established processes, for example by adding stabilizers such as sugar, sugar alcohols or other polyols, and/or lactic acid or other organic acids.

The disclosure also relates to the fermentation broth, fermentation supernatant or fermentation concentrate, of the host cell of the present disclosure.

The disclosure also relates to use of the phospholipase C of the present disclosure in oil degumming. When used in oils degumming, the phospholipase C of the present disclosure has a specific enzyme activity improved by 83%, while its degumming ability per unit enzyme activity is not reduced, and the protein expression is substantially unchanged, as compared with the phospholipase C of the prior art. In general, the mutant greatly increased the total harvest of phospholipase C enzyme activity and reduced production costs.

The disclosure also relates to a method of degumming oils, the method uses the phospholipase C of the present disclosure or the composition of the present disclosure or the fermentation broth, fermentation supernatant and/or fermentation concentrate, of the host cell of the present disclosure for degumming oils.

When quantities, concentrations, or other values or parameters are given in the form of a list of ranges, preferred ranges, or preferred upper limit values and preferred lower limit values, it should be understood as disclosure of any particular range constituted by a combination of any of the preferred upper limit values or the upper limit of any of the ranges and any of the preferred lower limit values or the lower limit of any of the ranges, regardless of whether the particular range are disclosed specially. Unless otherwise indicated, where a value range is given herein, the range is intended to include its endpoints, as well as all integers and fractions within the range. When a range is used, it is undesirable to limit the range to the particular numerical values listed.

The following examples are provided to illustrate preferred embodiments. Those skilled in the art should understand that the technology described in the following examples represents a technology found by the inventor and functioned well in the implementation of the method disclosed herein, and therefore it may be considered as a preferred mode for implementation. However, according to the present disclosure, those skilled in the art will understand that many changes can be made in the described embodiments without departing from the spirit and scope of the methods disclosed herein, which will provide the same or similar results as the described embodiments.

EXAMPLES

Experimental Materials
Experimental Strains and Plasmids
Strains: *Pichia pastoris* SMD1168 (Invitrogen, Catalog No. C175-00), *E. coli* DH5a (TAKARA, Catalog No. D9057A).
Plasmids: pAO815 plasmid (Invitrogen, Catalog No. V180-20), pAO-mPLC plasmid (constructed herein), pAO-m2PLC plasmid (constructed herein).
2. Media and Solutions
LB liquid medium: 0.5% yeast extract, 1% tryptone, 1% NaCl, pH 7.0.

LB solid medium: 1.5% agar added to the LB liquid medium.
YPD liquid medium: 1% yeast extract, 2% peptone, 2% glucose.
YPD solid medium: 2% agar added to the LB liquid medium.
MGYS solid medium: 1.34% yeast nitrogen base (YNB) containing ammonium sulfate without amino acids, 1% glycerol, 1M sorbitol, $4\times10^{-5}$% D-biotin, 2% agar.
BMM-soybean phospholipid screening medium: 1.34% yeast nitrogen base (YNB) containing ammonium sulfate without amino acids, $4\times10^{-5}$% D-biotin, 0.5% methanol (added after sterilization), 2% soybean phospholipid emulsion, 0.1M citric acid-sodium citrate buffer at pH 6.6, 2% agar, 10 uM $ZnSO_4.7H_2O$.
2% Soybean phospholipid emulsion: 2 g soybean phospholipid, 100 ml $H_2O$, homogenized with high speed homogenizer at 8000 rpm for 1 min.
BMGY liquid medium: 1% yeast extract, 2% peptone, 1.34% yeast nitrogen base (YNB) containing ammonium sulfate without amino acids, 1% glycerin, $4\times10^{-5}$% D-biotin, 0.1M potassium dihydrogen phosphate-dipotassium hydrogen phosphate buffer at pH 6.0.
BMMY liquid medium: 1% yeast extract, 2% peptone, 1.34% yeast nitrogen base (YNB) containing ammonium sulfate without amino acids, 0.3% $ZnSO_4.7H_2O$, 0.5% methanol (added after sterilization sterilized), $4\times10^{-5}$% D-Biotin (added after sterilization), 0.1M citric acid-sodium citrate buffer at pH 6.6.
Reaction buffer for detection of PLC activity by p-nitrophenylphosphorylcholine (pNPPC) method: 0.1M boric acid-sodium borate buffer (pH 7.6), 20 mM pNPPC, 1% Triton-X-100, 1 mM $CaCl_2$.
Restriction enzymes HindIII, SalI, EcoRI (purchased from New England Biotechnology (Beijing) Co., Ltd.)
PCR enzyme: TaKaRa Taq, PrimeSTAR®HS DNA polymerase (purchased from TaKaRa Bio (Dalian) Co., Ltd.)
T4 DNA ligase (purchased from Fermentas Co., Ltd.)

Example 1

Construction of Expression Vector pAO-mPLC

The variant BC-PC-PLC sequence mPLC (see SEQ ID NO: 1) with Y56H, N63D, N131S and N134D mutations was synthesized by gene synthesis (Shanghai Sangon Biotech Co., Ltd.). An about 750 bp fragment was amplified by PCR using PrimeSTAR®HS DNA polymerase and primer pair PLC-F/PLC-R (see Table 1). The pAO-mPLC vector was constructed by cloning the about 750 bp fragment into pAO815 through HindIII and EcoRI digestion sites.

TABLE 1

Primer sequences

| Primer name | Sequence |
|---|---|
| PLC-F | CTGAAGCTTGGTCAGCTGAGGACAAGCAT (SEQ ID NO: 5) |
| PLC-R | CCGGAATTCTTACCTGTCACCGTAAGTGTCGAACCATA (SEQ ID NO: 6) |

Example 2 pAO-mPLC Mutant Library Construction and Screening

A library of mutated amplicon fragments (each about 755 bp) was obtained by error-prone PCR (additional 0.3 mM MnCl$_2$ was added during PCR) using TaKaRa Taq enzyme, primers PLC-F/PLC-R (see Table 1), and the pAO-mPLC vector as templates. The obtained fragments were cloned into pAO815 through HindIII and EcoRI digestion sites, and the resulted vectors were transformed into E. coli DH5α, resulting in 1×10$^4$ mutants in total.

Each 1×10$^3$ pAO-mPLC mutants were washed with 2 ml sterile water and added into 8 ml of LB liquid medium (containing 100 μg/ml ampicillin), then cultured at 37° C. for 4 hours. The plasmid was extracted, then linearized by restriction enzyme SalI, and a fragment of about 8.5 kb was recovered. 500 ng of Vectors (using as little DNA as possible to ensure that most positive clones contain a single copy of the PLC gene) were transformed into competent cells of Pichia pastoris SMD1168 by electrotransformation. The transformants were inoculated on MGYS plates and cultured at 30° C. for 3 days to obtain a library of pAO-mPLC Pichia pastoris mutants. Monoclonal strains were selected and transferred from the plate to a BMM-soybean phospholipid screening plate. A clone strain having a large white precipitation circle was selected and named m2, see FIG. 1.

Example 3

Sequence Analysis of pAO-mPLC Mutant

The m2 strain was inoculated in 3 ml YPD liquid medium and cultured overnight at 30° C., then from which genomic DNAs were extracted. DNA sequence of the PLC in the m2 strain was amplified by PCR using PrimeSTAR®HS DNA polymerase, primers PLC-F/PLC-R (see Table 1), and the genomic DNAs of m2 strain as templates. The obtained sequence was sequenced by Shanghai Sangon Biotech Co., Ltd., using primers PLC-F/PLC-R (see Table 1). DNA sequencing of m2 PLC showed that one base was mutated, leading that glycine at 10 was mutated to aspartic acid (GGT→GAT).

Example 4

Construction of Expression Vector pAO-m2PLC

The variant BC-PC-PLC sequence m2PLC (see SEQ ID NO: 3) with G10D, Y56H, N63D, N131S and N134D mutations was synthesized by gene synthesis (Shanghai Sangon Biotech Co., Ltd.). A 750 bp fragment was amplified by PCR using PrimeSTAR®HS DNA polymerase and primer pair PLC-F/PLC-R (see Table 1). The pAO-m2PLC vector was constructed by cloning the about 750 bp fragment into pAO815 through HindIII and EcoRI digestion sites.

Example 5

Construction and Screening of Pichia pastoris Strains Expressing Phospholipase C Variants Expression vectors were constructed according to the processes described in Example 1 and Example 2. The expression vectors were linearized by the restriction enzyme SalI, and fragments of about 8.5 kb were recovered from gel. Competent cells of Pichia pastoris SMD1168 strain were prepared by LiAC method, and then 500 ng linearized expression vectors were transformed into the SMD1168 competent cells by electrotransformation. The transformants were inoculated on MGYS plates and cultured at 30° C. for 3 days. Monoclonal strains were selected and transferred from the plate to a BMM-soybean phospholipid screening plate. Clone strains having large white precipitation circles were selected, and then corresponding strains expressing the phospholipase C variants were obtained.

Example 6

Fermentation and Enzyme Activity Detection of the Pichia pastoris Strains Expressing the Phospholipase C Variants Two strains expressing the phospholipase C variants were inoculated in BMGY medium after being activated in liquid YPD, then the strains were cultured overnight at 30° C. with shaking at 220 rpm. The culture was transferred to BMMY liquid medium with an initial OD600 of 6. Induction was carried out by 2% methanol, and additional 1% methanol was added after 24 h, 32 h, 48 h and 56 h, respectively. Samples were taken at 72 h. The obtained supernatant samples were concentrated by 10-fold by ultrafiltration desalting with ultrafiltration tubes having a molecular weight cut-off of 10 kDa.

Determination of protein concentration: 1 μL of the concentrated enzyme solution was diluted by 10-fold with 50 mM PBS buffer (pH 6.0). 10 μL was used to react with Bradford reagent (Shanghai Sangon Biotech Co., Ltd.). After resting at room temperature for 10 min, the mixture was measured for the increase of OD600 light absorption.

Detecting phospholipase C activity by pNPPC method: two clean centrifuge tubes were used, one for sample and the other for blank control. 600 μL of reaction buffer was added to each centrifuge tube, and 25 μL of the concentrated enzyme solution was added in the sample tube but not the blank control tube. The two tubes were placed in a constant temperature water bath at 37° C. for 15 minutes, and 500 μL of absolute ethanol was added immediately to terminate the reaction. 25 μL of the enzyme solution to be tested was added to the blank tube, which was detected for the absorbance at 405 nm, and used to correct the zero point.

Definition of lipase enzyme activity unit: at 37° C. and pH 7.6, the amount of the enzyme that catalyzes the substrate to release 1 μmol phosphocholine over 1 min is 1 phospholipase activity unit (U).

The protein concentration in the fermentation broth of the mutant strain in the shaken flask was detected with Bradford reagent to obtain the specific enzyme activity. As shown in Table 2, the specific enzyme activity of m2PLC is higher than that of mPLC by 83%, and the protein expression is substantially not reduced.

Figure 2:
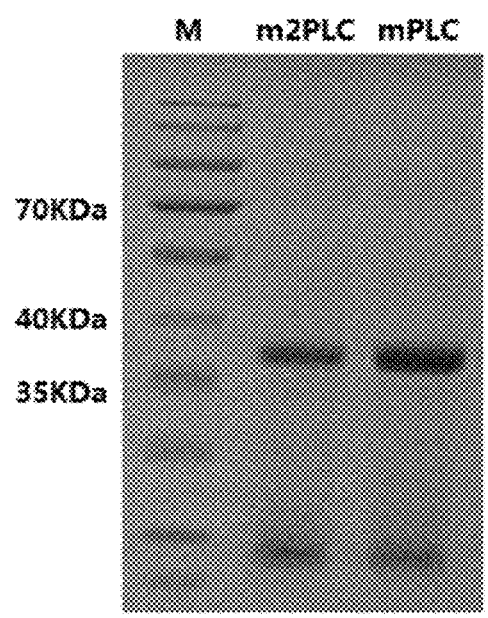
FIG. 2 is the SDS-PAGE protein electrophoresis diagram of phospholipase C variants in equal enzyme activity.

SDS-PAGE protein electrophoresis: SDS-PAGE electrophoresis in equal enzyme activity was performed according to the apparent enzyme activity of the concentrated enzyme solution. Based on the apparent enzyme activity of the mPLC enzyme solution, the m2PLC enzyme solution was diluted with water to the same enzyme activity as mPLC, and loaded in equal volume. The results are shown in FIG. 2. The results show that if electrophoresis was performed by loading samples with equal enzyme activity, the band concentration of the phospholipase C of m2PLC was significantly lower than that of mPLC, which was substantially consistent with the data of detected specific enzyme activities.

TABLE 2

Comparison of specific enzyme activities of phospholipase C variants

| Strains | Protein concentration (mg/L) | Apparent enzyme activity (U) | Specific enzyme activity (U/mg) |
| --- | --- | --- | --- |
| mPLC | 19 ± 1 | 10 ± 2 | 0.53 |
| m2PLC | 18.5 ± 0.9 | 18 ± 3 | 0.97 |

Example 7

Degumming Tests of Phospholipase C Variants 100 g soybean crude oil was heated to 55° C., and the enzyme solution with the same enzyme activity unit (based on the enzyme activity unit of 200 ppm mPLC) of the phospholipase C variant was added. DSM commercial enzyme Purifine® was used as a control. The system was made to contain 3% water phase, and sheared at high speed (10000 rpm) for 1 min by a high-speed shear. The reaction was stirred at 750 rpm at 55° C. for 2 h, and then the temperature was raised to 85° C. for 5 min. The sample was centrifuged at 12000 rpm for 10 min, and about 10 g of the upper oil was used to detect DAG content by HPLC.

Figure 3:
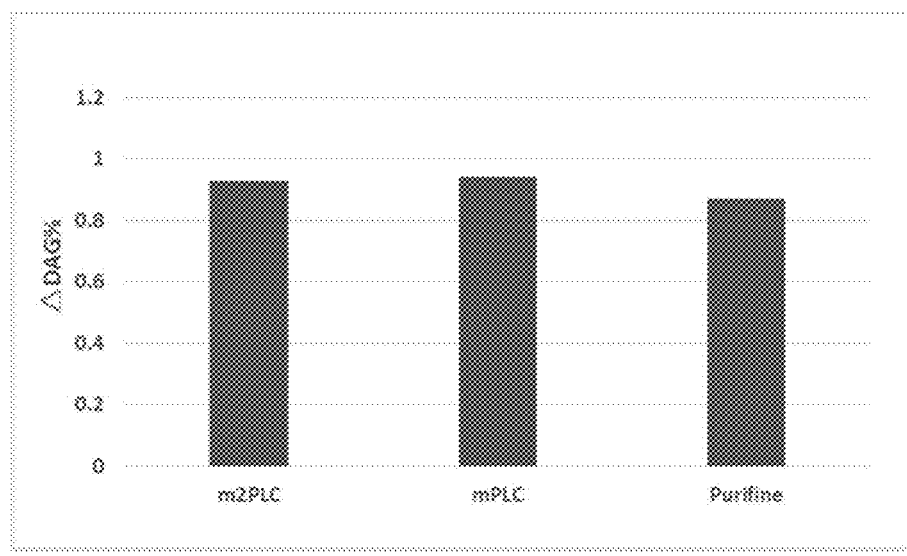
FIG. 3 shows the results of degumming experiments using phospholipases mPLC, m2PLC and Purifine®.

The increase in DAG of mPLC sample, m2PLC sample and control as compared to crude oil are shown in FIG. 3. The results show that when the enzyme solution of the same enzyme activity is added (i.e., smaller amount of m2PLC protein is used), the increase in DAG of m2PLC degumming is the same with that of mPLC, and slightly higher than that of DSM commercial enzymes Purifine®.

Conclusion

Compared with the sequence before mutation, m2PLC increased the specific enzyme activity by 83%, with its degumming ability per unit enzyme activity not decreased, and the protein expression substantially unchanged. In general, the mutant greatly increased the total harvest of phospholipase C enzyme activity and reduced production costs.

What is claimed is:

1. A phospholipase C mutant comprising or consisting of a sequence selected from:
   (a) the amino acid sequence of SEQ ID NO: 4, and
   (b) an amino acid sequence derived from *Bacillus cereus* and having at least 95% homology to the sequence of SEQ ID NO: 4, with the amino acid residue at position 10 being aspartic acid, the amino acid residue at position 56 of the amino acid sequence is histidine, the amino acid residue at position 63 of the amino acid sequence is aspartic acid, the amino acid residue at position 131 of the amino acid sequence is serine, and the amino acid residue at position 134 of the amino acid sequence is aspartic acid.

2. The phospholipase C mutant of claim 1, wherein the amino acid sequence of (b) has at least 98% homology to the sequence of SEQ ID NO: 4.

3. A composition comprising the phospholipase C mutant of claim 1.

4. A fermentation supernatant or a fermentation supernatant concentrate, comprising the phospholipase C mutant of claim 1.

5. A composition comprising the fermentation supernatant and/or the fermentation supernatant concentrate of claim 4.

6. A method for oil degumming, wherein the method uses the phospholipase C mutant of claim 1 for the oil degumming.

7. A method for oil degumming, wherein the method uses the fermentation broth, the fermentation supernatant and/or the fermentation supernatant concentrate, of claim 4 for the oil degumming.

* * * * *

SEQUENCE LISTING

```
<160> NUMBER OF SEQ ID NOS: 6

<210> SEQ ID NO 1
<211> LENGTH: 738
<212> TYPE: DNA
<213> ORGANISM: Artificial sequence
<220> FEATURE:
<223> OTHER INFORMATION: Phospholipase C

<400> SEQUENCE: 1
tggtcagctg aggacaagca taaggaaggt gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgatcatga aaacccctat     180
tacgatgaca gtaccttcgc ttctcacttt tacgatccag acaacggaaa gacatatatc     240
ccattcgcca agcaagctaa ggagactgga gctaagtact tcaagttggc tggagagtca     300
tacaagaata aagacatgaa gcaggccttc ttttatcttg ggttgtcatt gcattatttg     360
ggcgatgtca accaacctat gcatgccgca tcctttacgg acctgtccta tccacagggt     420
tttcactcca agtacgagaa ctttgtcgat actattaaag acaactacaa agttaccgat     480
gggaacggat attggaattg gaaaggcacc aaccctgaag aatggattca cggtgcagca     540
gtagttgcaa aacaggacta ctctggaatt gtcaatgaca ataccaaaga ttggttttgtg    600 aaagccgcag tctcccagga atatgcagat aaatggagag ctgaagttac acctatgact    660
ggtaaacgac taatggatgc ccaaagagtt actgctggtt acattcaatt atggttcgac    720
acttacggtg acaggtaa                                                   738

<210> SEQ ID NO 2
<211> LENGTH: 245
<212> TYPE: PRT
<213> ORGANISM: Artificial sequence
<220> FEATURE:
<223> OTHER INFORMATION: Phospholipase C

<400> SEQUENCE: 2

Trp Ser Ala Glu Asp Lys His Lys Glu Gly Val Asn Ser His Leu Trp
```

```
1               5                   10                  15
Ile Val Asn Arg Ala Ile Asp Ile Met Ser Arg Asn Thr Thr Leu Val
                20                  25                  30
Lys Gln Asp Arg Val Ala Gln Leu Asn Glu Trp Arg Thr Glu Leu Glu
                35                  40                  45
Asn Gly Ile Tyr Ala Ala Asp His Glu Asn Pro Tyr Asp Asp Ser
 50                  55                  60
Thr Phe Ala Ser His Phe Tyr Asp Pro Asp Asn Gly Lys Thr Tyr Ile
 65                  70                  75                  80
Pro Phe Ala Lys Gln Ala Lys Glu Thr Gly Ala Lys Tyr Phe Lys Leu
                85                  90                  95
Ala Gly Glu Ser Tyr Lys Asn Lys Asp Met Lys Gln Ala Phe Phe Tyr
                100                 105                 110
Leu Gly Leu Ser Leu His Tyr Leu Gly Asp Val Asn Gln Pro Met His
                115                 120                 125
Ala Ala Ser Phe Thr Asp Leu Ser Tyr Pro Gln Gly Phe His Ser Lys
 130                 135                 140
Tyr Glu Asn Phe Val Asp Thr Ile Lys Asp Asn Tyr Lys Val Thr Asp
 145                 150                 155                 160
Gly Asn Gly Tyr Trp Asn Trp Lys Gly Thr Asn Pro Glu Glu Trp Ile
                165                 170                 175
His Gly Ala Ala Val Val Ala Lys Gln Asp Tyr Ser Gly Ile Val Asn
                180                 185                 190
Asp Asn Thr Lys Asp Trp Phe Val Lys Ala Ala Val Ser Gln Glu Tyr
                195                 200                 205
Ala Asp Lys Trp Arg Ala Glu Val Thr Pro Met Thr Gly Lys Arg Leu
                210                 215                 220
Met Asp Ala Gln Arg Val Thr Ala Gly Tyr Ile Gln Leu Trp Phe Asp
 225                 230                 235                 240
Thr Tyr Gly Asp Arg
                245

<210> SEQ ID NO 3
<211> LENGTH: 738
<212> TYPE: DNA
<213> ORGANISM: Artificial sequence
<220> FEATURE:
<223> OTHER INFORMATION: Phospholipase C

<400> SEQUENCE: 3
tggtcagctg aggacaagca taaggaagat gtgaatagtc acttatggat cgtgaaccgt      60
gccattgata taatgtctag gaatacaact ctggttaagc aagatagagt tgctcaattg     120
aatgaatggc gtacagagct agagaatggc atctacgctg ctgatcatga aaaccccta t    180 tacgatgaca gtaccttcgc ttctcacttt tacgatccag acaacggaaa gacatatatc     240
ccattcgcca agcaagctaa ggagactgga gctaagtact tcaagttggc tggagagtca     300
tacaagaata agacatgaa gcaggccttc ttttatcttg ggttgtcatt gcattatttg      360
ggcgatgtca accaacctat gcatgccgca tcctttacgg acctgtccta tccacagggt     420
tttcactcca gtacgagaa ctttgtcgat actattaaag acaactacaa agttaccgat      480
gggaacggat attggaattg gaaaggcacc aaccctgaag aatggattca cggtgcagca     540
gtagttgcaa acaggacta ctctggaatt gtcaatgaca ataccaaaga ttggtttgtg      600
aaagccgcag tctcccagga atatgcagat aaatggagag ctgaagttac acctatgact     660
```

```
ggtaaacgac taatggatgc ccaaagagtt actgctggtt acattcaatt atggttcgac    720
acttacggtg acaggtaa                                                  738
```

<210> SEQ ID NO 4
<211> LENGTH: 245
<212> TYPE: PRT
<213> ORGANISM: Artificial sequence
<220> FEATURE:
<223> OTHER INFORMATION: Phospholipase C

<400> SEQUENCE: 4

```
Trp Ser Ala Glu Asp Lys His Lys Glu Asp Val Asn Ser His Leu Trp
1               5                   10                  15

Ile Val Asn Arg Ala Ile Asp Ile Met Ser Arg Asn Thr Thr Leu Val
            20                  25                  30

Lys Gln Asp Arg Val Ala Gln Leu Asn Glu Trp Arg Thr Glu Leu Glu
        35                  40                  45

Asn Gly Ile Tyr Ala Ala Asp His Glu Asn Pro Tyr Tyr Asp Asp Ser
    50                  55                  60

Thr Phe Ala Ser His Phe Tyr Asp Pro Asp Asn Gly Lys Thr Tyr Ile
65                  70                  75                  80

Pro Phe Ala Lys Gln Ala Lys Glu Thr Gly Ala Lys Tyr Phe Lys Leu
                85                  90                  95

Ala Gly Glu Ser Tyr Lys Asn Lys Asp Met Lys Gln Ala Phe Phe Tyr
            100                 105                 110

Leu Gly Leu Ser Leu His Tyr Leu Gly Asp Val Asn Gln Pro Met His
        115                 120                 125

Ala Ala Ser Phe Thr Asp Leu Ser Tyr Pro Gln Gly Phe His Ser Lys
    130                 135                 140

Tyr Glu Asn Phe Val Asp Thr Ile Lys Asp Asn Tyr Lys Val Thr Asp
145                 150                 155                 160

Gly Asn Gly Tyr Trp Asn Trp Lys Gly Thr Asn Pro Glu Glu Trp Ile
                165                 170                 175

His Gly Ala Ala Val Val Ala Lys Gln Asp Tyr Ser Gly Ile Val Asn
            180                 185                 190

Asp Asn Thr Lys Asp Trp Phe Val Lys Ala Ala Val Ser Gln Glu Tyr
        195                 200                 205

Ala Asp Lys Trp Arg Ala Glu Val Thr Pro Met Thr Gly Lys Arg Leu
    210                 215                 220

Met Asp Ala Gln Arg Val Thr Ala Gly Tyr Ile Gln Leu Trp Phe Asp
225                 230                 235                 240

Thr Tyr Gly Asp Arg
                245
```

<210> SEQ ID NO 5
<211> LENGTH: 29
<212> TYPE: DNA
<213> ORGANISM: Artificial sequence
<220> FEATURE:
<223> OTHER INFORMATION: Forward primer

<400> SEQUENCE: 5

```
ctgaagcttg gtcagctgag gacaagcat                                      29
```

<210> SEQ ID NO 6
<211> LENGTH: 38
<212> TYPE: DNA
<213> ORGANISM: Artificial sequence

```
<220> FEATURE:
<223> OTHER INFORMATION: Reverse primer

<400> SEQUENCE: 6
ccggaattct tacctgtcac cgtaagtgtc gaaccata                              38
```